(12) United States Patent
Cox

(10) Patent No.: US 8,530,642 B2
(45) Date of Patent: *Sep. 10, 2013

(54) PARTICULATE-SOLUBLE GLUCAN PREPARATION

(75) Inventor: Donald J. Cox, Maple Grove, MN (US)

(73) Assignee: Biopolymer Engineering, Inc., Eagan, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/180,290

(22) Filed: Jul. 11, 2011

(65) Prior Publication Data

US 2012/0065157 A1    Mar. 15, 2012

Related U.S. Application Data

(63) Continuation of application No. 12/151,666, filed on May 8, 2008, now Pat. No. 7,981,447.

(60) Provisional application No. 60/916,690, filed on May 8, 2007.

(51) Int. Cl.
*C07H 1/00* (2006.01)

(52) U.S. Cl.
USPC .................................. 536/123.12; 536/123.1

(58) Field of Classification Search
None
See application file for complete search history.

(56) References Cited

U.S. PATENT DOCUMENTS

| 6,323,338 B1 | 11/2001 | Potter et al. | |
|---|---|---|---|
| 6,369,216 B1 * | 4/2002 | Patchen et al. | 536/123.12 |
| 6,485,945 B1 | 11/2002 | Potter et al. | |
| 2003/0165604 A1 | 9/2003 | Tsubaki et al. | |
| 2004/0082539 A1 | 4/2004 | Kelly | |

FOREIGN PATENT DOCUMENTS

| WO | WO 91/03495 | 3/1991 |
|---|---|---|
| WO | WO 96/28476 | 9/1996 |

OTHER PUBLICATIONS

U.S. Appl. No. 60/916,690, filed May 8, 2007, Cox, Donald J.
International Preliminary Report on Patentability for PCT Patent Application No. PCT/US08/05914 mailed Nov. 10, 2009; 5 pgs.
International Search Report and Written Opinion for PCT Patent Application No. PCT/US08/05914 mailed Aug. 1, 2008; 10 pgs.

* cited by examiner

*Primary Examiner* — Patrick Lewis

(74) *Attorney, Agent, or Firm* — Mueting, Raasch & Gebbardt, P.A.

(57) ABSTRACT

Particulate β-glucan is solubilized at elevated pressure and temperature to form particulate-soluble β-glucan. The particulate-soluble β-glucan is capable of being dried to a powder form and subsequently re-solubilized.

10 Claims, 4 Drawing Sheets

PARTICULATE-SOLUBLE GLUCAN PREPARATION

This application is a continuation of U.S. application Ser. No. 12/151,666 filed May 8, 2008, issued as U.S Pat. No. 7,981,447, which claims the benefit of U.S. Provisional Application No. 60/916,690, entitled SOLUBLE GLUCAN PREPARATION, filed May 8, 2007.

BACKGROUND OF THE INVENTION

The present invention relates to a particulate-soluble β-glucan. More particularly, the present invention relates to an improved method and composition of particulate-soluble β-glucan.

Glucans are generally described as polymers of glucose and are derived from yeast, bacteria, fungi and plants such as oats and barley. Glucans containing a β(1-3)-linked glucopyranose backbone are known to have biological activity, specifically, they have been shown to modulate the immune system and more recently to induce hematopoietic stem and progenitor cell (HSPC) mobilization.

In the past, a high quality soluble β-glucan was expensive to produce. The expense made it cost prohibitive as a nutritional supplement or food ingredient, for example. Therefore, there is a need for an improved soluble β-glucan.

SUMMARY OF THE INVENTION

Particulate β-glucan is solubilized in an acidic solution at elevated temperature and pressure. The resulting soluble β-glucan may be further clarified and purified using, for example, centrifugation and/or chromatographic techniques. The resulting product, even when comprised of high molecular weight glucans, can be dried to a powder and subsequently re-solubilized.

BRIEF DESCRIPTION OF THE DRAWINGS

FIG. 5 is a graphic representation of TNFa production induced by various β-glucans.

DETAILED DESCRIPTION OF THE INVENTION

Figure 1:
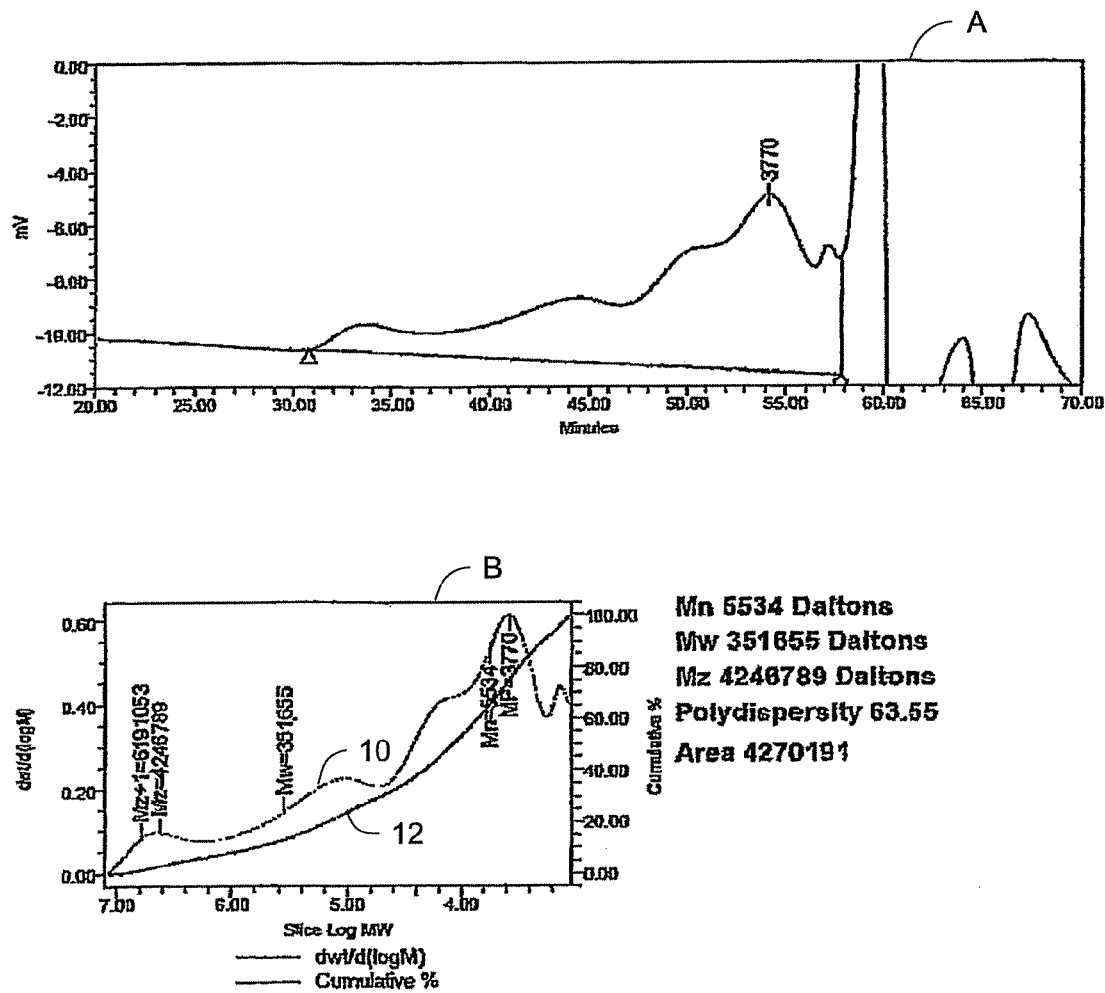
FIGS. 1-4 are RI traces and data transformations graphs of particulate-soluble β-glucan samples.

The starting material used in the present invention is particulate, or insoluble, β-glucan, produced by any method. The particulate β-glucan starting material may range in size from whole glucan particles down to submicron-sized particles. The level of impurities within the starting material may also vary. However, as the level of impurities within the starting material increases, the amount of soluble glucan recovered decreases. One example of suitable starting material is WGP 3-6® from Biothera.

Any of a number of source of b-glucan can be used for the present invention. Examples of such sources are yeast, barely, oats, mushrooms and other fungi, etc.

The particulate β-glucan is treated with acid under pressure and elevated temperature to produce soluble β-glucan. To begin, pelleted, particulate β-glucan is resuspended and mixed in a sealable reaction vessel in a buffer solution and brought to pH 3.6. Buffer reagents are added such that every liter, total volume, of the final suspension mixture contains about 0.61 g sodium acetate, 5.24 ml glacial acetic acid and 430 g pelleted, particulate β-glucan. The vessel is purged with nitrogen to remove oxygen and increase the pressure within the reaction vessel.

Typically, the pressure inside the vessel is brought to 35 PSI, and the suspension is heated to about 135° C. for up to about 5.5 hours. It was found that under these conditions the β-glucan will solubilize. As the temperature decreases from 135° C., the amount of solubilization also decreases.

It should be noted that this temperature and pressure are optimized for the embodiment just described. Optimization and adjustment of temperatures and pressures may be required if any of the reaction conditions and/or reagents are altered.

The increased pressure and temperature imparts advantages over prior art processes for solubilizing β-glucan by virtually eliminating the use of hazardous chemicals from the process. Hazardous chemicals that have previously been used include, for example, flammable VOCs such as ether and ethanol, very strong acids such as formic acid and sulphuric acid and caustic solutions of very high pH. The present process is not only safer, but, by reducing the number of different chemicals used and the number of steps involved, is more economical.

An additional advantage of the present process is that the length of the above treatment controls the molecular weight of the resulting particulate-soluble β-glucan. As the term is used throughout, "particulate-soluble β-glucan" may be in any of the soluble, particulate or re-solubilized forms. The length of treatment time is inversely related to the resulting molecular weight size. In other words, as the treatment time increases, the resulting average molecular weight of the particulate-soluble β-glucan decreases. This principal is illustrated in the following.

Four samples were collected from a batch of particulate-soluble β-glucan suspension at various time-points (60, 90, 120 and 240 min.) during the above-described process. The molecular weights of the samples were determined by size exclusion chromatography against dextran molecular weight markers. The results are summarized in Table 1.

TABLE 1

| Sample Time | Mn* | Mw** | Mz*** | Hexose Conc. |
|---|---|---|---|---|
| 60 min. | 5,500 | 352,000 | 4,250,000 | 5.16 mg/ml |
| 90 min. | 8,500 | 1,180,000 | 5,430,000 | 12.33 mg/ml |
| 120 min. | 6,600 | 354,000 | 2,730,000 | 11.26 mg/ml |
| 240 min. | 5,100 | 56,500 | 362,000 | ≈25 mg/ml |

*number average molecular weight calculated by:

$$\overline{M}n = \frac{\Sigma_i N_i M_i}{\Sigma_i N_i}$$

**weight average molecular weight calculated by:

$$\overline{M}w = \frac{\Sigma_i N_i M_i^2}{\Sigma_i N_i M_i}$$

where $N_i$ is the number of molecules of molecular weight $M_i$.

***z-averaged molecular weight, which is based on the volume of the polymer chains.

As evidenced by the above data, the particulate β-glucan slowly begins to breakdown with the largest average size occurring at about 90 min. After the 90 min. time-point, the average size decreases. Time-point specific data is shown in FIGS. 1-4.

FIG. 1 includes panels A and B. Panel A is a refractive index (RI) trace of the 60 min. sample. In panel B, a section of the data generated in panel A was transformed and plotted on the graph shown. Curve 10 represents the transformed raw data. Curve 12 represents the cumulative percentage of specific molecular weights. Molecular weight was determined by a standard curve generated with dextran of known size (data not shown).

Figure 2:
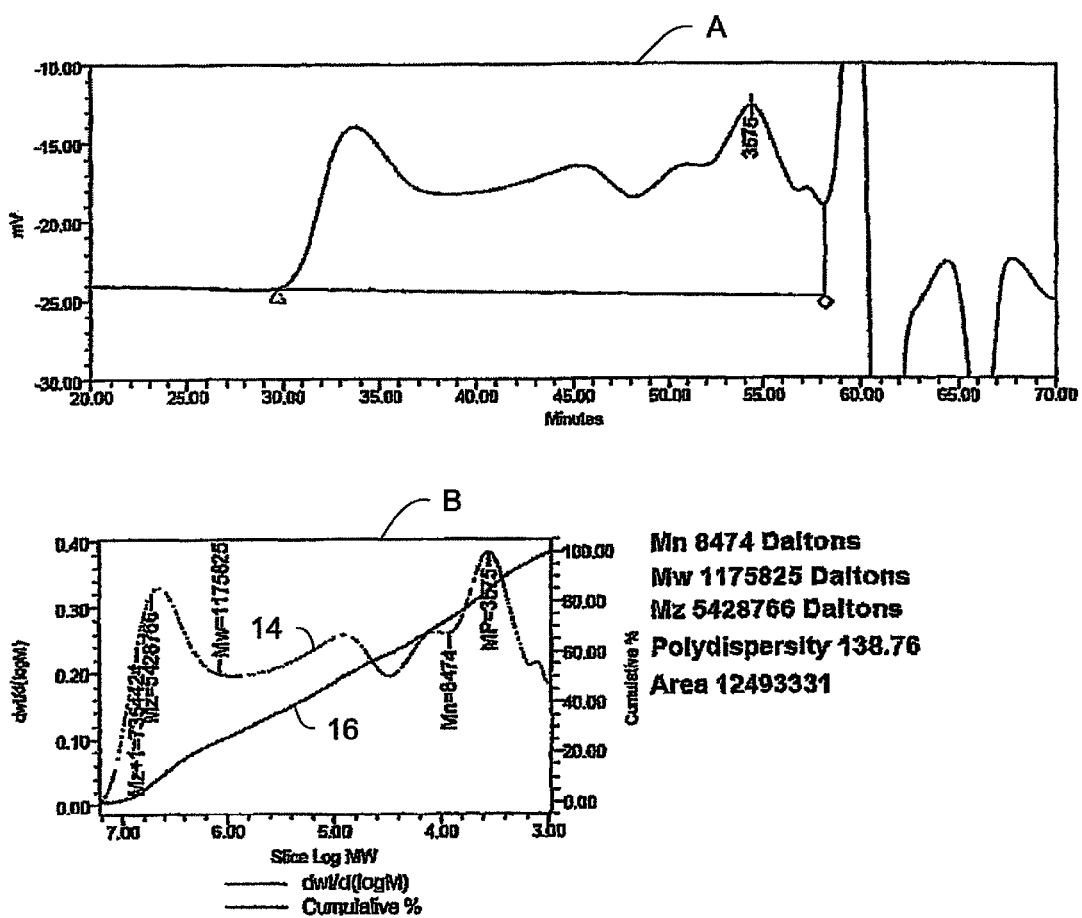

Data generated from the 90 min. sample is shown in FIG. 2. Panel A and panel B, with curves 14 and 16, correspond to the panels A and B of FIG. 1.

Figure 3:
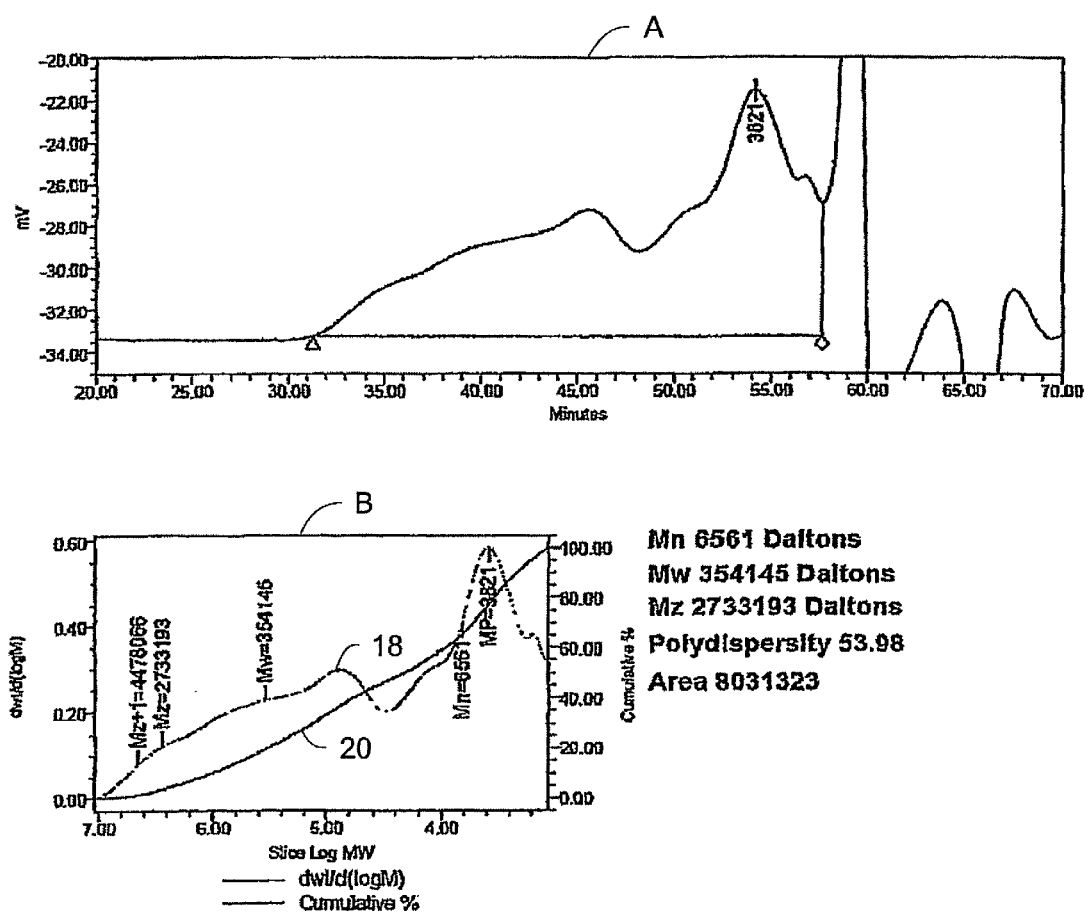

Data generated from the 120 min. sample is shown in FIG. 3. Panel A and panel B, with curves 18 and 20, correspond to the panels A and B of FIG. 1.

Figure 4:
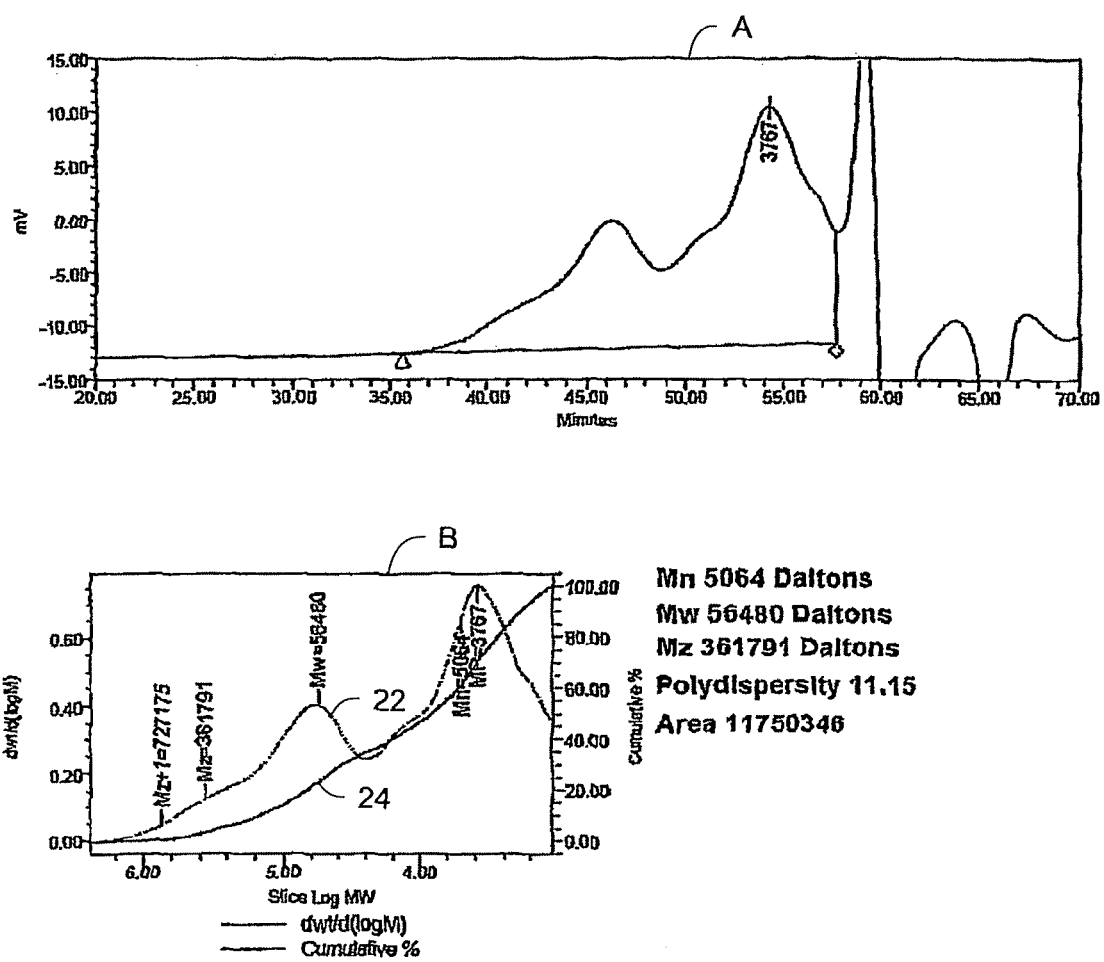

Data generated from the 240 min. sample is shown in FIG. 4. Panel A and panel B, with curves 22 and 24, correspond to the panels A and B of FIG. 1.

Specific sizes of particulate-soluble glucan may be more useful for specific applications. For example, when applied topically, molecules of smaller molecular weight may better penetrate skin. Larger molecular weight molecules, on the other hand, may be better suited for oral administration. Therefore, the ability to easily control the average size of the glucan molecules offers a significant competitive advantage.

The exact duration of heat treatment is typically determined experimentally by sampling reactor contents. Various tests may be performed such as gel permeation chromatography (GPC) analyses. The process maximizes the yield of particulate-soluble material that meets specific specification profiles and impurity levels. Once the β-glucan is solubilized, the mixture is cooled to stop the reaction.

The particulate-soluble β-glucan may be washed and utilized at this point, however, for pharmaceutical applications further purification is typically performed. Any combination of one or more of the following steps may be used to further purify and/or clarify the particulate-soluble β-glucan. Other means known in the art may also be used if desired. Suitable means include, for example, centrifugation or continuous-flow centrifugation, which eliminates a significant amount of lipid impurities.

In some instances, the inclusion of lipids within the particulate-soluble β-glucan may increase its effectiveness against certain infectious diseases or enhancing the immune system. The process presented here provides a means to effectively control and vary the amount of lipid in the particulate-soluble β-glucan composition.

Alternatively or in addition to, the particulate-soluble β-glucan may be filtered. In one embodiment, the material is filtered through a 0.2 μm filter.

Chromatography may also be used for purification. The particulate-soluble β-glucan may be conditioned at some point in preparation for chromatography. For example, if a chromatographic step includes hydrophobic interaction chromatography (HIC), the particulate-soluble β-glucan can be conditioned to the appropriate conductivity and pH with a solution of ammonium sulphate and sodium acetate. A suitable solution is 3.0 M ammonium sulfate, 0.1 M sodium acetate, which is used to adjust the pH to 5.5.

Another chromatographic step that may be utilized is gel permeation chromatography (GPC). Multiple chromatography cycles may be needed to ensure that the load does not exceed the capacity of the column.

At this point, the particulate-soluble β-glucan is purified and ready for use. The particulate-soluble β-glucan that is generally collected has an average molecular weight>1,000,000 Da, with a high polydispersity. An advantage of this particulate-soluble β-glucan product, especially in the high molecular weight ranges such as over a million Daltons (Da), is that the product can be spray dried to a powder form and then subsequently re-solubilized in solutions of pH about 5 and higher—essentially from weakly acidic to strongly basic. In addition, re-solubilization occurs at temperatures as low as about room temperature (~25° C.). Depending on the final concentration after re-solubilization and the solvent used, the time and temperature requirements for re-solubilization will vary.

The product's ability to re-solubilize makes it ideal for creating an instantized form of β-glucan suitable for, for example, instant drink powders. Briefly, particulate-soluble β-glucan in dry form is re-wet to achieve a moisture content of about 9%-12%, which forms an agglomerate. A surfactant, such as lecithin, is added to the agglomerate via a two-fluid nozzle. The concentration of surfactant will vary depending on the surfactant used and the conditions and solvent into which the product will be finally dissolved. The agglomerate is then run through three stages of a fluid bed drier. The first stage heats the product, the second stage conditions the product and the third stage cools the product. The resulting product is sifted to form the instantized product.

Another way to form an instantized product is through the addition of a second dry-form soluble ingredient such as table sugar or salt (NaCl). In one example, 200 mg of powdered, particulate-soluble β-glucan and about 0.5 to about 1.0 g of sucrose crystals were mixed and ground in a mortor bowl for about 2-3 minutes. The mixture was added to 500 mls of room temperature water and shook vigorously. The particulate-soluble β-glucan re-solubilized. An identical experiment was carried out with NaCl with the same result.

The particulate-soluble β-glucan product, whether in its solubilized, powdered or re-solubilized form, may be used for any of a number of applications. Particulate-soluble β-glucan is ideal for use as a nutritional supplement, a food ingredient, a cosmetic ingredient and a pharmaceutical product for use in humans and agricultural/companion/exotic animals.

Typical foods in which the dry or wet forms of particulate-soluble β-glucan may be added include, for example, cereals and cereal products, baked goods and baking mixes, beverages and beverage bases, dairy product analogs such as soy milk, milk and milk products, plant protein products, processed fruits and fruit juices, soft candy, soup and soup mixes, yogurt, bottled water and drinks, nutrition bars, etc. Various masking agents and other additives may be added to improve the flavor and texture if necessary.

In its liquid form, the particulate-soluble β-glucan can be used to make edible films. A thin layer of liquid product is dried by any of a number of means known in the art. Additives may be added to the liquid product to create films of various textures or to make them more or less pliable. The films are useful as carriers for pharmaceutical or supplement products. Here again, various masking agents can be added to improve the flavor of the film.

The particulate-soluble β-glucan product may also be more efficacious than prior art particulate β-glucan. For example, the product may be more effective against infectious diseases or cancer. Increased efficacy may be in terms of better uptake, better immune system enhancement, decreased dosing regiments, etc.

To this end, in vitro studies showed that the particulate-soluble β-glucan does not induce TNFα from human peripheral blood mononuclear cells (PBMC) at concentrations up to 300 μg/mL. Specifically, human PBMC were cultured in cRPMI medium containing 5% heat-inactivated FCS. Cells were stimulated with various beta glucans (all endotoxin free), TLR7/8 agonist, or vehicle. The beta glucans were used at various concentrations. After overnight incubation at 37° C., 5% $CO_2$, cell-free supernatants were collected, stored at −20° C. until cytokine analysis by ELISA. The results from three replicates are shown in FIG. 5. As evidenced by the graph, whole glucan particles stimulate TNFα production, while the particulate-soluble product does not. Because TNFα is a major cytokine involved in an inflammatory response, the particulate-soluble product is not expected to induce an inflammatory response.

While this invention has been shown and described with references to particular embodiments, it will be understood by those skilled in the art that various changes in form and detail may be made therein without departing from the spirit and scope of the invention encompassed by the appended claims.

The invention claimed is:

1. A composition comprising a dried particulate-soluble β-glucan derived from yeast capable of being solubilized in a solution having a pH of about 5 or more.

2. The composition of claim 1 wherein the particulate-soluble β-glucan is instantized.

3. The composition of claim 2 and further comprising:
a second dry-form soluble ingredient.

4. The composition of claim 1 wherein the particulate-soluble β-glucan is capable of being re-solubilized in a solution at a temperature of about room temperature or higher.

5. A composition comprising a dried particulate-soluble β-glucan derived from yeast capable of being solubilized in a solution having a temperature of about 25° C. or more.

6. The composition of claim 5 wherein the particulate-soluble b-glucan has an average molecular weight of over about 1,000,000 Da.

7. The composition of claim 1 wherein the particulate-soluble β-glucan has an average molecular weight of over about 1,000,000 Da.

8. The composition of claim 5 wherein the particulate-soluble β-glucan is instantized.

9. The composition of claim 8 and further comprising:
a second dry-form soluble ingredient.

10. The composition of claim 5 wherein the solution has a pH of about 5 or more.

* * * * *

UNITED STATES PATENT AND TRADEMARK OFFICE
CERTIFICATE OF CORRECTION

PATENT NO. : 8,530,642 B2
APPLICATION NO. : 13/180290
DATED : September 10, 2013
INVENTOR(S) : Donald J. Cox Page 1 of 1

It is certified that error appears in the above-identified patent and that said Letters Patent is hereby corrected as shown below:

In the Claims

In column 6, claim 6, line 8, please delete "b-glucan" and insert --β-glucan--.

Signed and Sealed this
Second Day of December, 2014

Michelle K. Lee
*Deputy Director of the United States Patent and Trademark Office*